United States Patent [19]

Rodriguez et al.

[11] 4,271,172
[45] Jun. 2, 1981

[54] 6-AMINO-SPIRO[PENAM-2,4'-PIPERIDINE]-3-CARBOXYLIC ACIDS, ANTIBACTERIAL COMPOSITIONS THEREOF AND METHOD OF USE THEREOF

[75] Inventors: Ludovic Rodriguez, Brussels; Jacques Leclercq, Braine l'Alleud; Pierre Ykman; Eric Cossement, both of Brussels, all of Belgium

[73] Assignee: U C B Societe Anonyme, Saint-Gilles-lez-Bruxelles, Belgium

[21] Appl. No.: 162,616

[22] Filed: Jun. 24, 1980

[30] Foreign Application Priority Data

Jun. 25, 1979 [GB] United Kingdom ............... 22054/79

[51] Int. Cl.³ .................. C07D 499/76; A61K 31/43; C07D 499/74; C07D 499/58
[52] U.S. Cl. ..................................... 424/267; 546/17; 548/147; 260/245.2 R
[58] Field of Search .......................... 546/17; 548/147; 424/267; 260/245.2

[56] References Cited

U.S. PATENT DOCUMENTS

| 4,091,027 | 5/1978 | Rodriguez et al. ................. 548/147 |
| 4,137,236 | 1/1979 | Rodriguez et al. ................. 548/147 |
| 4,137,628 | 2/1979 | Rodriguez et al. ................. 548/147 |
| 4,145,343 | 3/1979 | Rodriguez et al. ................. 548/147 |

Primary Examiner—Robert T. Bond
Attorney, Agent, or Firm—Wenderoth, Lind & Ponack

[57] ABSTRACT

6-Amino-spiro[penam-2,4'-piperidine]-3-carboxylic acids, salts and esters thereof of the formula

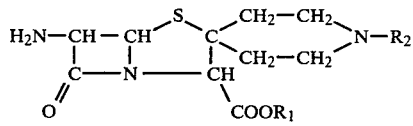

wherein $R_1$ is hydrogen, benzyl or an alkali metal or ammonium ion and $R_2$ is methyl, phenyl or benzyl and process for preparing the same.

These compounds are useful as intermediates in the synthesis of a new group of antibiotics having properties similar to penicillins, besides own antibiotic activity with a broad antibacterial spectrum. Therefore, they are useful as antibacterials agents and as therapeutic agents for humans and for animals in the treatment of infectious diseases caused by Gram-positive and Gram-negative bacteria.

6 Claims, No Drawings

6-AMINO-SPIRO[PENAM-2,4'-PIPERIDINE]-3-CARBOXYLIC ACIDS, ANTIBACTERIAL COMPOSITIONS THEREOF AND METHOD OF USE THEREOF

The present invention relates to new 6-amino-spiro[penam-2,4'-piperidine]-3-carboxylic acids, salts and esters thereof and also to the preparation and use thereof.

The new 6-amino-spiro[penam-2,4'-piperidine]-3-carboxylic acids are compounds analogous to the 6-aminopenicillanic acids, in which the carbon atom in the 2-position of the "penam" ring (see definition hereinbelow) is substituted by a 3-azepentamethylene chain, which forms with this carbon atom a heterocycle. Therefore, these compounds comprise a spiro-heterocycle constituted by the penam ring and by a saturated monocyclic heterocycle having one nitrogen atom i.e. a piperidine ring.

These compounds are the precursors of new penicillins, which are the subject matter of our Application Ser. No. 162,615, filed 24 June 1980. However, they also exhibit an antibiotic activity of their own with a broad antibacterial spectrum, which is far from negligible when compared with that of the corresponding 6-amino-penicillanic acid.

The new compounds of the present invention are 6-amino-spiro[penam-2,4'-piperidine]-3-carboxylic acids having the general formula:

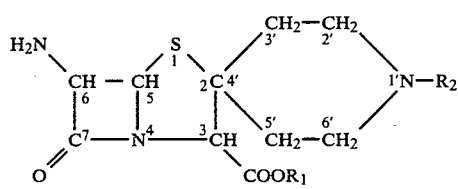

wherein $R_1$ is a hydrogen atom or a benzyl radical or an alkali metal or ammonium ion and $R_2$ is a methyl, phenyl or benzyl radical, as well as the addition salts thereof with pharmaceutically acceptable inorganic or organic acids.

In view of the existence of three asymmetric carbon atoms at $C_3$, $C_5$ and $C_6$, these compounds can occur in the form of a mixture of 8 isomers which can be grouped into 4 racemic diasteroisomers. In fact, the kinetics of reactions leads to the formation of only 3 of these racemates, namely, the alpha, beta and gamma racemates. The alpha-racemate, one of the optical antipodes of which has a configuration corresponding to that of penicillin, is preferably isolated from the reaction mixture.

In the present specification, the nomenclature used is that proposed by R. J. Stoodley in "Progress in Organic Chemistry" 8, (1973), 102–103. In particular, the following ring system is designated "penam":

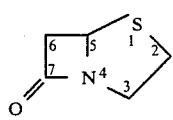

The compounds of general formula (I) are prepared by a multi-stage process, which comprises:

(1) reacting tert-butyl 2-formyl-2-phthalimido-acetate of formula (II) with an alpha-amino-4-mercapto-1-$R_2$-4-piperidineacetic acid of formula (III) to give the gamma-isomer of a tert-butyl 4-carboxy-alpha-phthalimido-8-$R_2$-1-thia-3,8-diazaspiro[4.5]decane-2-acetate of formula (IV), in accordance with the equation:

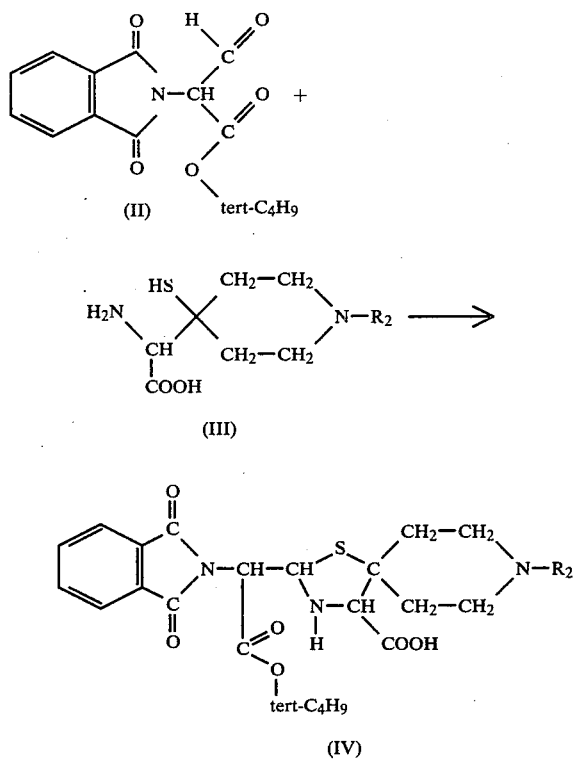

(2) epimerizing the gamma-isomer of formula (IV) to the alpha-isomer of formula (V) by heating the pyridine or with diethylamine, in accordance with the equation:

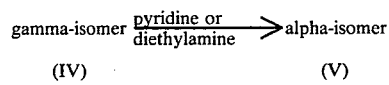

(3) preparing the tert-butyl 4-benzyloxycarbonyl-alpha-phthalimido-8$R_2$-1-thia-3,8-diazaspiro[4.5]decane-2-acetate of formula (VI) by reacting the alpha-isomer of formula (V) with diazophenylmethane or with a benzyl halide, in accordance with the equation:

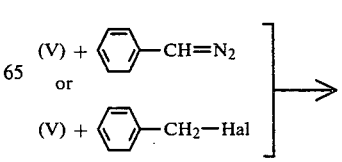

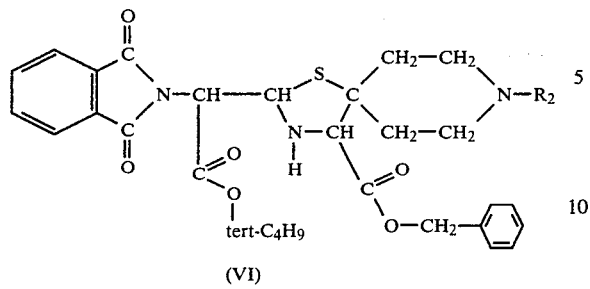

(VI)

(4) subjecting the compound of formula (VI) to dephthalimidation by hydrazinolysis, to give a tert-butyl alpha-amino-4-benzyloxycarbonyl-8-$R_2$-1-thia-3,8-diazaspiro[4.5]decane-2-acetate of formula (VII), in accordance with the equation:

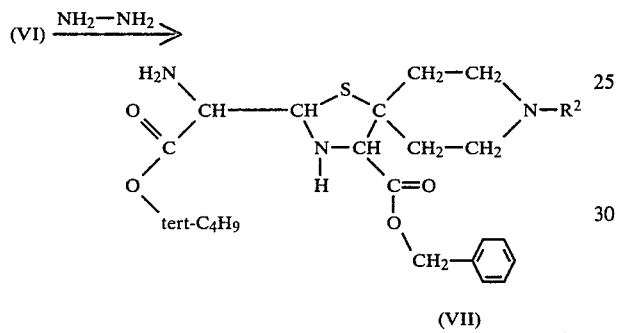

(VII)

(5) selectively dealkylating the tert-butyl ester group of compound (VII) by treating it in solution in nitromethane with gaseous hydrogen chloride to give alpha-amino-4-benzyloxycarbonyl-8-$R_2$-1-thia-3,8-diazaspiro[4.5]-decane-2-acetic acid dihydrochloride of formula (VIII) in accordance with the equation:

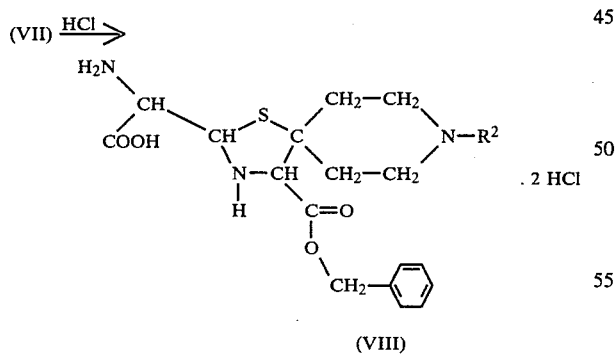

(VIII)

(6) blocking the alpha-amino group of compound (VIII) by means of trityl chloride to give 4-benzyloxycarbonyl-8-$R_2$-alpha-trítylamino-1-thia-3,8-diazaspiro[4.5]-decane-2-acetic acid of formula (IX) in accordance with the equation:

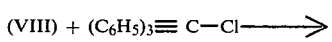

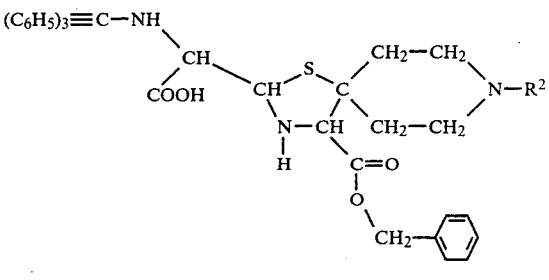

(IX)

(7) cyclizing the compound of formula (IX), preferably at an elevated temperature, by reaction with a carbodiimide (abbreviated to CI), to give a benzyl 1'-$R_2$-6-tritylamino-spiro[penam-2,4'-piperidine]-3-carboxylate of formula (X) in accordance with the equation:

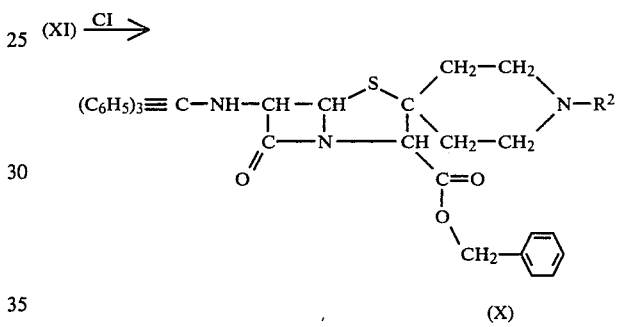

(X)

(8) treating the compound of formula (X) with p-toluenesulfonic acid (p-TS) to give a benzyl 6-amino-1'-$R_2$-spiro[penam-2,4'-piperidine]-3-carboxylate of formula (I), in the form of a di-p-toluenesulfonate, in accordance with the equation:

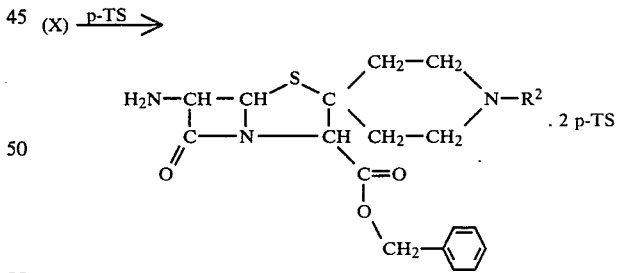

(I) with $R_1$=benzyl and, (9) when it is desired, subjecting the compound thus obtained of formula (I), wherein $R_1$ is a benzyl radical, to hydrogenolysis to give a corresponding 6-amino-1'-$R_2$-spiro[penam-2,4'-piperidine]-3-carboxylic acid of formula (I), in the form of a di-p-toluenesulfonate, in accordance with the equation:

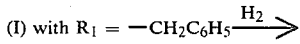

-continued

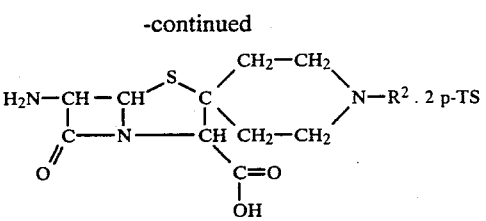

(I) with $R_1=H$

In the above general formulae, $R_2$ is a methyl, phenyl or benzyl radical.

It is clear that, in order to obtain compounds of formula (I) wherein $R_1$ is a benzyl radical and $R_2$ is a methyl, phenyl or benzyl radical, it is sufficient to perform only steps (1) to (8) of the above-described process.

To obtain the compounds of formula (I) wherein $R_1$ is an alkali metal or ammonium ion and $R_2$ is a methyl, phenyl or benzyl radical, the 6-amino-1'-$R_2$-spiro[penam-2,4'-piperidine]-3-carboxylic acid obtained in step (9) is neutralized with an alkali metal hydroxide or ammonia in known manner.

The preparation of tert-butyl 2-formyl-2-phthalimido-acetate of formula (II) is described in the literature (J. Sheenan et al., J. Am. Chem. Soc. 76, (1954), 158–160).

The preparation of an alpha-amino-4-mercapto-1-$R_2$-4-piperidineacetic acid of formula (III) may be performed in the following manner:

(a) reacting ethyl 2-isocyanoacetate with a 1-$R_2$-4-piperidone in the presence of a suspension of sodium hydride in tetrahydrofuran to give ethyl alpha-formamido-1-$R_2$-piperidine-$\Delta^{4,alpha}$-acetate in accordance with the equation:

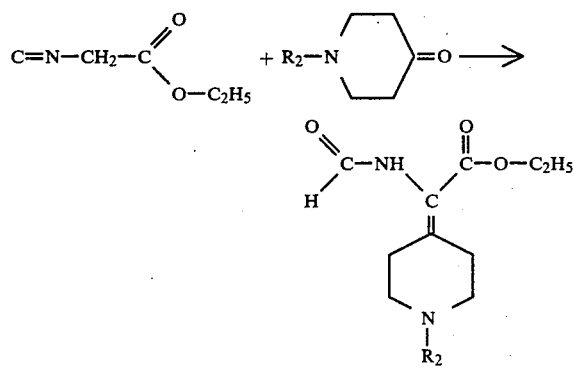

(b) heating ethyl alpha-formamido-1-$R_2$-piperidine-$\Delta^{4,alpha}$-acetate under reflux with phosphorus pentasulfide in solution in acetonitrile to give ethyl 8-$R_2$-1-thia-3,8-diazaspiro[4.5]dec-2-ene-4-carboxylate in accordance with the equation:

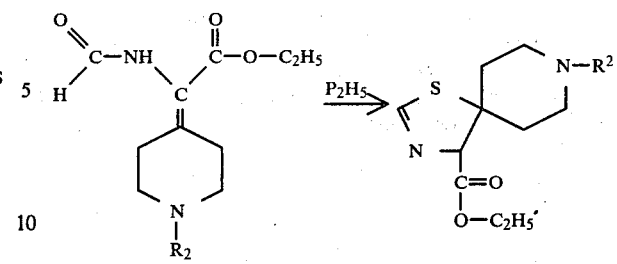

(c) decyclizing ethyl 8-$R_2$-1-thia-3,8-diazaspiro[4.5]dec-2-ene-4-carboxylate by heating with aqueous hydrochloric acid, to give the desired alpha-amino-4-mercapto-1-$R_2$-4-piperidineacetic acid of formula (III) in the form of a dihydrochloride in accordance with the equation:

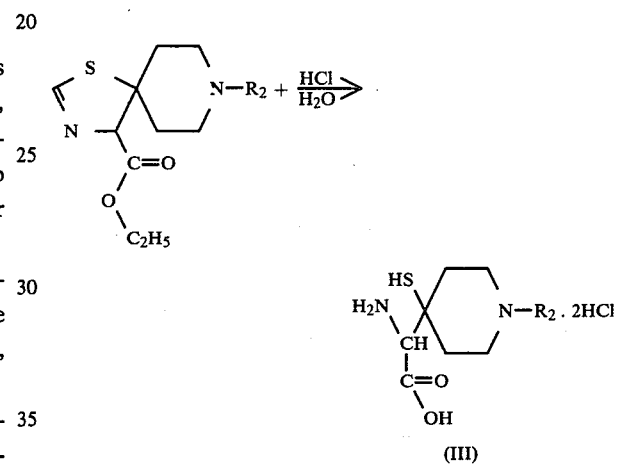

$R_2$ being a methyl, phenyl or benzyl radical in all these formulae.

If desired, the two enantiomeric forms of the compounds of formula (III) can be separated, thus making it possible to obtain the optically pure diastereoisomer (IV) directly.

USE OF THE NEW COMPOUNDS OF THE PRESENT INVENTION

The interest of the new compounds of the present invention lies in the fact that they lead, by simple and known reactions, to a new series of compounds which are analogous to the penicillins. These compounds differ structurally from the known penicillins by the presence of a nitrogen-containing saturated monocyclic heterocycle in the 2-position, in place of a gem-dimethyl substituent. These novel compounds have the general formula:

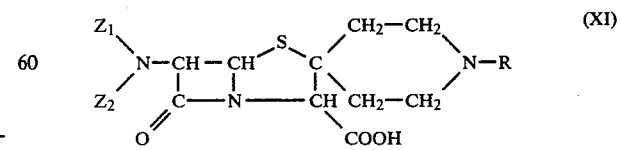

wherein R is a methyl, phenyl or benzyl group ($R=R_2$ as defined hereinbefore).

These compounds, processes for preparing the same and uses thereof are the subject matter of our U.S. Pat.

application Ser. No. 162,615, filed June 24 1980, to which reference is made for a more detailed description.

The substituents $Z_1$ and $Z_2$ are conventional substituents known from the chemistry of the penicillins, such as those described for example, in Ullmanns Encyklopädie der technischen Chemie, 4th Edition, vol. 7, (1974), 651-652.

By way of example, it is possible to obtain from the compounds of the present invention, the acids of general formula (XI), wherein $Z_1$ is a hydrogen atom and $Z_2$ is a 2-phenylacetyl radical (see Example 2 hereinafter) or a 2,6-dimethoxybenzoyl, 5-methyl-3-phenyl-4-isoxazole-carbonyl or 2-amino-2-phenylacetyl radical, or $Z_1$ and $Z_2$ together form a bivalent radical $Z_3$, preferably the (hexahydro-1H-azepin-1-yl)methylene radical, and also the pharmaceutically acceptable non-toxic salts thereof.

The compounds of general formula (XI), wherein $Z_1$ is a hydrogen atom and $Z_2$ has the same meaning as above, are obtained by subjecting the compounds of the present invention to an acylation reaction with a compound of formula $Z_2Y$, wherein $Z_2$ has the same meaning as above and Y is a halogen atom or a hydroxyl group.

Where the initial compound used to prepare the compounds of general formula (XI) is a 6-amino-spiro[penam-2,4'-piperidine]-3-carboxylic acid of general formula (I), wherein $R_1$ is a benzyl radical, the synthesis of the compounds of general formula (XI) obviously comprises a second step, which consists in the hydrogenolysis of the benzyl esters obtained to give the corresponding acids.

The compounds of formula $Z_2Y$ used as acylating agents for the amino group in the 6-position may be acid halides (Y=halogen) or free acids (Y=OH); in this latter case, the acylation operation is performed in the presence of a coupling agent, for example a carbodiimide, such as diisopropylcarbodiimide. Furthermore, where the compounds of formula $Z_2Y$ contain a free amino group, the latter may be protected in known manner, for example by a benzyloxycarbonyl radical, which is subsequently eliminated during the hydrogenolysis step.

Thus, in order to introduce the $Z_2$ radicals previously mentioned, for example, it is possible to use, as acylating agent, phenylacetyl chloride, 2,6-dimethoxybenzoyl chloride, 5-methyl-3-phenyl-4-isoxazolecarbonyl chloride or N-(benzyloxycarbonyl)-D(−)-2-phenylglycine.

By "pharmaceutically acceptable non-toxic salts" there are to be understood, more particularly, metal salts, such as sodium, potassium, calcium and aluminum salts, ammonium salts and salts of amines such as the trialkylamines and more particularly triethylamine, procaine, dibenzylamine, N-benzyl-beta-phenethylamine, L-ephenamine, N,N'-dibenzyl-ethylenediamine, dehydroabietylamine, N,N'-bis-dehydroabietyl-ethylenediamine and the N-(lower alkyl)-piperidines, such as N-ethylpiperidine and, more generally, the salts already known for penicillins G and V (see Ullmanns Encyklopädie, loc.cit., p. 653). These salts can be obtained from the corresponding acids in known manner.

Where, in general formula (XI), the radical $Z_2$ is, for example, the 2-amino-2-phenylacetyl radical, the compounds can also be in the form of addition salts with pharmaceutically acceptable acids, such as acetic, citric, succinic, ascorbic, hydrochloric, hydrobromic, sulfuric or phosphoric acids.

The compounds of general formula (XI), wherein $Z_1$ and $Z_2$ represent a bivalent radical $Z_3$, are obtained from the compounds of the present invention by reaction with an activated derivative of a compound of the formula $Z_3=O$, $Z_3$ having the same meaning as above. Thus, for example, where the radical $Z_3$ is the (hexahydro-1H-azepin-1-yl)methylene radical, a 6-aminospiro[penam-2,4'-piperidine]-3-carboxylic acid or one of its esters is reacted with an activated derivative of hexahydro-1H-azepine-1-carboxaldehyde. The activated derivatives of the compounds $Z_3=O$ are generally the corresponding amide chlorides obtained by reaction with oxalyl chloride or the complex obtained by reaction with dimethyl sulfate.

The compounds of general formula (XI) and the pharmaceutically acceptable non-toxic salts thereof are used as antibacterial agents, or dietetic supplements in animal feeds and as therapeutic agents for man and animals in the treatment of infectious diseases caused by Gram-positive or Gram-negative bacteria.

These compounds have a very broad spectrum of antibacterial activity both against Gram-positive and Gram-negative bacteria but they are most particularly effective for combating resistant strains of bacteria which produce beta-lactamases.

In particular, they have antibacterial activities which are superior to those of the corresponding penicillins, as is demonstrated by comparative tests described in the above-mentioned patent application, filed concurrently herewith, to which reference is made for a more detailed description.

The following Examples are given for the purpose of illustrating the present invention Preparation of the alpha-amino-4-mercapto-1-$R_2$-4-piperidineacetic acids of general formula (III).

Step (a)

a.1. Ethyl alpha-formamido-1-methyl-piperidine-$\Delta^{4,alpha}$-acetate.

Into a suspension of 24.35 g of approximately 5% sodium hydride in 635 ml of dry tetrahydrofuran is introduced a solution of 57.4 g (0.51 mole) of ethyl 2-isocyanoacetate and of 57.4 g (0.51 mole) of 1-methyl-4-piperidone in 380 ml of tetrahydrofuran, with vigorous stirring at ambient temperature. Stirring is continued for three hours and the reaction mixture is left to stand overnight. After evaporating excess solvent in vacuo, the residue is treated cautiously with a solution of 76 g of glacial acetic acid in 634 ml of water. When decomposition is achieved, the reaction mixture is rendered alkaline with sodium carbonate and extracted with dichloromethane. After evaporating the solvent, 53.5 g of ethyl alpha-formamido-1-methyl-piperidine-$\Delta^{4,alpha}$-acetate is obtained. Yield: 46.6%; M.P. 116°-117° C. (recrystallized from ethyl acetate).

Thin layer chromatography on silica: 1 spot.

Analysis for $C_{11}H_{18}N_2O_3$ (M.W. 226.281): calculated (%): N 12.38; found (%): 12.31 a.2. Ethyl 1-benzyl-alpha-formamido-piperidine-$\Delta^{4,alpha}$-acetate.

The preparation is the same as in a.1., except that the 1-methyl-4-piperidone is replaced by the corresponding quantity of 1-benzyl-4-piperidone and the dichloromethane may also be replaced by benzene. Yield: 60%; M.P. 87°-88° C. (recrystallized from ethyl acetate).

Thin layer chromatography on silica: 1 spot.

Analysis for $C_{17}H_{22}N_2O_3$ (M.W. 302.379); calculated (%): C 67.77; H 7.33; N 9.26; found (%): C 66.77; H 7.29; N 8.94 a.3. Ethyl alpha-formamido-1-phenyl-piperidine-$\Delta^{4,alpha}$-acetate.

The preparation is the same as in a.1., except that the 1-methyl-4-piperidone is replaced by the corresponding quantity of 1-phenyl-4-piperidone. The reaction mixture is stirred for 1 hour at ambient temperature, then the temperature is increased to 40° to 45° C. Subsequently, the reaction mixture is stirred for 3 hours at ambient temperature and finally left to stand overnight.

Yield: 59%; M.P. 135°-136° C. (recrystallized from ethyl acetate).

Analysis for $C_{16}H_{20}N_2O_3$ (M.W. 288.34): calculated (%): C 66.64; H 6.99; N 9.72; found (%): C 67.89; H 6.87; N 9.75

Step (b)

b.1. Ethyl 8-methyl-1-thia-3,8-diazaspiro[4.5]dec-2-ene-4-carboxylate.

11.1 g of phosphorus pentasulfide are added all at once to a solution of 56.6 g (0.25 mole) of ethyl alpha-formamido-1-methyl-piperidine-$\Delta^{4,alpha}$-acetate in 265 ml of acetonitrile. After heating the reaction mixture under reflux for 1.5 hours, it is cooled and filtered. The filtrate is then evaporated and the residue is taken up in 500 ml of benzene. It is filtered, again evaporated to dryness and distilled twice to obtain finally ethyl 8-methyl-1-thia-3,8-diazaspiro[4.5]dec-2-ene-4-carboxylate in a yield of 40%; B.P. 115°-116° C./0.001 mm Hg.

Infra-red spectrum (film): 1750 cm$^{-1}$ (ester)

Analysis for $C_{11}H_{18}N_2O_2S$ (M.W. 242.326): calculated (%): C 54.52; H 7.49; N 11.56; S 13.23; found (%): C 54.36; H 7.37; N 11.53; S 12.91 b.2. Ethyl 8-benzyl-1-thia-3,8-diazaspiro[4.5]dec-2-ene-4-carboxylate.

This product is prepared in the same way as in b.1., but starting with ethyl 1-benzyl-alpha-formamido-piperidine-$\Delta^{4,alpha}$-acetate, by heating a solution of this compound, before the addition of the phosphorus pentasulfide, and heating the reaction mixture under reflux for only 45 minutes.

The residue is passed through a column of silica gel (Merck 60), using chloroform as eluent, to give ethyl 8-benzyl-1-thia-3,8-diazaspiro[4.5]dec-2-ene-4-carboxylate in a yield of 33%; M.P. 67°-68° C.

Infra-red spectrum (KBr): 1742 cm$^{-1}$ (ester)

Mass spectrum: M$^+$· m/e = 318

Analysis for $C_{17}H_{22}N_2O_2S$ (M.W. 318.445): calculated (%): C 64.12; H 8.96; N 8.80; S 10.07; found (%): C 65.78; H 7.14; N 8.54; S 9.52 b.3. Ethyl 8-phenyl-1-thia-3,8-diazaspiro[4.5]dec-2-ene-4-carboxylate.

22.3 g (0.10 mole) of phosphorus pentasulfide are added all at once under an atmosphere of nitrogen, to a solution of 144 g (0.5 mole) of ethyl alpha-formamido-1-phenylpiperidine-$\Delta^{4,alpha}$-acetate in 600 ml of acetonitrile, heated to 60° to 65° C. The reaction mixture is heated under reflux for 90 minutes. A further 11 g of phosphorus pentasulfide are then added and heating under reflux continued for 30 minutes. The reaction mixture is then cooled and evaporated almost to dryness. The residue is taken up in 1 liter of benzene, decanted and extraction repeated twice with 500 ml of benzene. The benzene phases are combined and evaporated to dryness, there being obtained 111 g of crude ethyl 8-phenyl-1-thia-3,8-diazaspiro[4.5]dec-2-ene-4-carboxylate which is used in stage c) without further purification.

Mass spectrum: M$^+$·m/e = 304.

Step (c)

c.1. alpha-Amino-4-mercapto-1-methyl-4-piperidineacetic acid dihydrochloride.

A solution of 113 g (0.466 mole) of ethyl 8-methyl-1-thia-3,8-diazaspiro-[4.5]dec-2-ene-4-carboxylate in 5 liters of approximately 6 N hydrochloric acid is heated under reflux for 4 hours. The solution is decolorized with activated charcoal and evaporated to dryness. Traces of water are eliminated by entrainment with benzene and isopropanol. The residue is then dissolved in 1.5 liter of ethanol, concentrated to a volume of approximately 400 ml and allowed to crystallize. In this way, 104.7 g of alpha-amino-4-mercapto-1-methyl-4-piperidine-acetic acid dihydrochloride is obtained; Yield: 81%; M.P. 201°-202° C. (decomposition).

Infra-red spectrum (KBr): 1730 cm$^{-1}$ (carbonyl)

With an aqueous solution of ferric chloride: dark blue coloration

Analysis for $C_8H_{16}N_2O_2S$. 2 HCl (M.W.: amino acid only = 204.298; dihydrochloride = 277.288): calculated (%): C 34.66; H 6.54; N 10.11; Cl$^{31}$ 25.58; found (%): C 34.38; H 6.63; N 10.14; Cl 25.97 c.2. alpha-Amino-1-benzyl-4-mercapto-4-piperidineacetic acid dihydrochloride.

The preparation is the same as in c.1. but starting from ethyl 8-benzyl-1-thia-3,8-diazaspiro[4.5]dec-2-ene-4-carboxylate. The product obtained is triturated with isopropyl alcohol and dried; Yield: 95%; M.P. 172°-174° C. (retains isopropyl alcohol).

Infra-red spectrum (KBr): 1730 cm$^{-1}$ (carboxyl)

Analysis for $C_{14}H_{20}N_2O_2S$. 2 HCl (M.W.: amino acid only = 280.386; dihydrochloride = 353.326): calculated (%): C 45.58; H 6.28; N 7.93; Cl$^{31}$20.07; S 9.07; found (%): C 46.18; H 6.37; N 7.47; Cl 19.31; S 8.28 c.3. alpha-Amino-4-mercapto-1-phenyl-4-piperidineacetic acid dihydrochloride.

A solution of 111 g of ethyl 8-phenyl-1-thia-3,8-diazaspiro[4.5]dec-2-ene-4-carboxylate, obtained as in b.3., is heated under reflux at 110° C. for 4 hours in 4 liters of 6N hydrochloric acid. The solution is decolorized with activated charcoal and then evaporated to dryness. Traces of water are eliminated by entrainment with 2 liters of benzene and 1 liter of isopropyl alcohol. The residue is taken up in 1 liter of diethyl ether. The crystals obtained are filtered off and dried. There are obtained 109.2 g of alpha-amino-4-mercapto-1-phenyl-4-piperidineacetic acid dihydrochloride. Yield: 64% (for the successive steps b.3 and c.3); M.P. 198°-200° C. (decomposition).

IR spectrum (KBr): 1725 cm$^{-1}$ (CO); 745 cm$^{-1}$ (phenyl).

Analysis for $C_{13}H_{18}N_2O_2S$. 2 HCl (M.W. 339.29): calculated (%): C 46.02; H 5.97; N 8.26; Cl$^-$20.90; found (%): C 43.6; H 6.15; N 7.60; Cl 20.63

Example 1. Preparation of 6-amino-spiro[penam-2,4'-piperidine]-3-carboxylic acids.

Step (1)

1.1. tert-Butyl 4-carboxy-8-methyl alpha-phthalimido-1-thia-3,8-diazaspiro[4.5]-decane-2-acetate (gamma-isomer).

To a solution of 166.9 g (0.57 mole) of tert-butyl 2-formyl-2-phthalimido-acetate in 1150 ml of ethanol, preheated to 60° C., there is added a solution of 160 g (0.57 mole) of alpha-amino-4-mercapto-1-methyl-4-piperidineacetic acid dihydrochloride and 235.6 g (1.73 mole) of sodium acetate (crystallized with three molecules of water) dissolved in 1150 ml of water. The reaction mixture is stirred for about ten minutes and then left to stand for 24 hours. The precipitate is filtered off, washed with water and dried. 223 g of the gamma-isomer of tert-butyl 4-carboxy-8-methyl-alpha-phthalimido-1-thia-3,8-diazaspiro-[4.5]decane-2-acetate is obtained; Yield: 81%; M.P. 276°–278° C. (decomposition).

Infra-red spectrum (KBr): 3290 cm$^{-1}$ (NH)

Analysis for $C_{23}H_{29}N_3O_6S$ (M.W. 475.575): calculated (%): C 58.09; H 6.15; N 8.84; S 6.74; found (%): C 58.19; H 6.20; N 8.48; S 6.71

1.2. tert-Butyl 8-benzyl-4-carboxy-alpha-phthalimido-1-thia-3,8-diazaspiro-[4.5]decane-2-acetate (gamma-isomer)

The preparation is the same as in 1.1. but starting from the corresponding quantity of alpha-amino-1-benzyl-4-mercapto-4-piperidineacetic acid dihydrochloride. The yield is 72% (in two crops). The mother liquors of the first crop are extracted with benzene and the evaporation residue is crystallized in ethyl acetate; M.P. 208°–209° C. (decomposition).

Infra-red spectrum (KBr or CHCl$_3$): 3300 cm$^{-1}$ (NH)

Analysis for $C_{29}H_{33}N_3O_6S$ (M.W. 551.673): calculated (%): C 63.12; H 6.02; N 7.61; S 5.81; found (%): C 60.92; H 6.06; N 7.80; S 5.62

1.3. tert-Butyl 4-carboxy-8-phenyl-alpha-phthalimido-1-thia-3,8-diazaspiro[4.5]-decane-2-acetate (gamma-isomer).

This compound is prepared by the process described in 1.1 but starting from the corresponding amount of alpha-amino-1-phenyl-4-mercapto-4-piperidine-acetic acid dihydrochloride. The product obtained is successively washed with water, cold ethanol and diethyl ether. Yield: 68%; M.P. 211°–213° C.

Infra-red spectrum (KBr): 3270 cm$^{-1}$ (NH), 1710 cm$^{-1}$ (carboxyl)

NMR spectrum (DMSO-TMS):

4 H (phthalyl): singlet at 8.0 ppm
5 H (phenyl): multiplet at 7.4 to 6.6 ppm
H$_{alpha}$: doublet at 5.2 ppm
10 H (piperidine+H$_2$+H$_4$): multiplet at 4.0 to 1.5 ppm
9 H (tert-butyl): singlet at 1.4 ppm
H$_{alpha}$ and H$_2$ are coupled, J=8.3 Hz.

Step (2)

2.1. tert-Butyl 4-carboxy-8-methyl-alpha-phthalimido-1-thia-3,8-diazaspiro[4.5]decane-2-acetate (alpha-isomer).

183.9 g (0.38 mole) of the gamma-isomer obtained in 1.1 is heated under reflux for 24 hours in 920 ml of pyridine. It is filtered while hot and the precipitate is washed with pyridine, then with diethyl ether and dried. After drying for 8 hours at 140° C. in a high vacuum, a first crop of 110 g (29.9%) of the alpha-isomer is obtained, melting at 278°–280° C. (decomposition).

The pyridine filtrate is concentrated to approximately 5 ml of pyridine per gram of product and the operation is repeated. After five such operations, the required alpha-isomer is obtained in a yield of 91.1%.

Infra-red spectrum (KBr): 3340 cm$^{-1}$ (NH)

Analysis for $C_{23}H_{29}N_3O_6S$ (M.W. 475.575): calculated (%): C 58.09; H 6.15; N 8.84; S 6.74; found (%): C 57.28; H 6.08; N 8.73; S 6.72

2.2. tert-Butyl 8-benzyl-4-carboxy-alpha-phthalimido-1-thia-3,8-diazaspiro[4.5]-decane-2-acetate (alpha-isomer)

123 g of the gamma-isomer obtained in 1.2 are heated under reflux for 6 hours in 2 liters of diethylamine and left to stand overnight. It is then filtered and the precipitate is washed with a little diethylamine and then with diethyl ether. The precipitate is dried, 103.9 g of the required alpha-isomer being obtained; Yield: 84.5%; M.P. 230°–232° C. (decomposition).

Infra-red spectrum (KBr): 3348 cm$^{-1}$ (NH)

NMR spectrum (CDCl$_3$-TMS): H$_4$: doublet at 4.2 ppm; coupled with amino H$_3$, J=12.5 Hz (the coupling withstands treatment with D$_2$O)

Mass spectrum: M+·m/e=551

Analysis for $C_{29}H_{33}N_3O_6S$ (M.W. 551.673) calculated (%): C 63.12; H 6.02; N 7.61; found (%): C 63.35; H 6.99; N 7.83

2.3. tert-Butyl 4-carboxy-8-phenyl-alpha-phthalimido-1-thia-3,8-diazaspiro[4.5]-decane-2-acetate (alpha-isomer).

127 g (0.236 mole) of the gamma-isomer obtained in 1.3 are heated for 8 hours at about 100° C. under an atmosphere of nitrogen in 700 ml of pyridine. The solution is then left to stand for 2 days in a refrigerator. The alpha-isomer crystallizes out. It is filtered off, washed several times with a cold mixture of acetone and hexane (2:8 v/v) and once with hexane alone. There are obtained 25 g of the desired alpha-isomer. As in 2.1, the operation may be repeated several times, finally to obtain an increased yield of the alpha-isomer; M.P. 229°–230° C. (decomposition).

IR spectrum (KBr): 3325 cm$^{-1}$ (NH)

Analysis for $C_{28}H_{31}N_3O_6S$ (M.W. 537.62): calculated (%): C 62.55; H 5.81; N 7.82; found (%): C 61.47; H 5.72; N 7.63

Step (3).

3.1. tert-Butyl 4-benzyloxycarbonyl-8-methyl-alpha-phthalimido-1-thia-3,8-diazaspiro[4.5]decane-2-acetate.

A suspension of 100 g (0.21 mole) of the alpha-isomer of tert-butyl 4-carboxy-8-methyl-alpha-phthalimido-1-thia-3,8-diazaspiro[4.5]decane-2-acetate obtained in 2.1 in 1.5 liter of chloroform is heated under reflux and an 0.41 molar solution of diazophenylmethane is introduced slowly into the chloroform with brisk agitation up to refusal (approximately 40% excess so as to obtain substantially complete esterification). After standing overnight, excess diazophenylmethane is decomposed by adding formic acid and the solution thus obtained is washed with a saturated aqueous solution of sodium hydrogen carbonate. The organic solution is dried over anhydrous sodium sulfate and then evaporated to dryness. After crystallization from acetonitrile, 94.6 g of tert-butyl 4-benzyloxycarbonyl-8-methyl-alpha-phthalimido-1-thia-3,8-diazaspiro[4.5]-decane-2-acetate are obtained: Yield: 79.6%; M.P. 173°–175° C.

Infra-red spectrum (KBr): 3340 cm$^{-1}$ (NH)

Thin layer chromatography on silica: 1 spot

NMR spectrum (CDCl$_3$-TMS): H$_4$: doublet at 3.72 ppm; coupled with amino H$_3$, J=13.3 Hz p Analysis for $C_{30}H_{35}N_3O_6S$ (M.W. 565.7) calculated (%): C 63.70; H 6.31; N 7.43; S 5.67; found (%): C 63.62; H 6.31; N 7.43; S 5.70

3.2. tert-Butyl 8-benzyl-4-benzyloxycarbonyl-alpha-phthalimido-1-thia-3,8-diazaspiro[4.5]decane-2-acetate.

The preparation is the same as in 3.1 but using the alpha-isomer of tert-butyl 8-benzyl-4-carboxy-alpha-phthalimido-1-thia-3,8-diazaspiro[4.5]-decane-2-acetate obtained in 2.2; Yield: 80%; M.P. 193°–193.5° C. (recrystallized from acetonitrile).

Thin layer chromatography on silica: 1 spot
Infra-red spectrum (KBr): 3345 cm$^{-1}$ (NH)
NMR spectrum (CDCl$_3$-TMS): H$_4$: doublet at 3.78 ppm; coupled with amino H$_3$; J=13.3 Hz

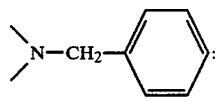

singlet at 3.45 ppm

Analysis for C$_{36}$H$_{39}$N$_3$O$_6$S (M.W. 641.798): calculated (%): C 67.37; H 6.13; N 6.55; found (%): C 66.86; H 6.07; N 6.48

3.3. tert-Butyl 4-benzyloxycarbonyl-8-phenyl-alpha-phthalimido-1-thia-3,8-diazaspiro[4.5]decane-2-acetate.

17 g (0.10 mole) of benzyl bromide, dissolved in 20 ml of N,N-dimethylformamide are added to 24 g (0.0447 mole) of the alpha-isomer of tert-butyl 4-carboxy-8-phenyl-alpha-phthalimido-1-thia-3,8-diazaspiro[4.5]decane-2-acetate, obtained in 2.3, dissolved in 200 ml of N,N-dimethylformamide. The reaction mixture is stirred overnight at ambient temperature and is then poured onto ice, extracted three times with 500 ml amounts of ethyl acetate and the organic phase washed successively with a little water, with a saturated aqueous solution of sodium hydrogen carbonate and again with a little water. The solution is then dried and evaporated to dryness. After recrystallization from ethyl acetate, there are obtained 18.8 g tert-butyl 4-benzyloxycarbonyl-8-phenyl-alpha-phthalimido-1-thia-3,8-diazaspiro[4.5]decane-2-acetate. Yield: 66%; M.P. 184°–185° C.

IR spectrum (KBr) in cm$^{-1}$: 3340 (NH); 1735, 1710 (CO); 750 (phenyl).

Analysis for C$_{33}$H$_{37}$N$_3$O$_6$S (M.W. 627.74): calculated (%): C 66.96; H 5.94; N 6.70; found (%): C 67.34; H 5.76; N 6.54

Step (4).

4.1. tert-Butyl alpha-amino-4-benzyloxycarbonyl-8-methyl-1-thia-3,8-diazaspiro-[4.5]decane-2-acetate.

To a solution of 113.2 g (0.2 mole) of tert-butyl 4-benzyloxycarbonyl-8-methyl-alpha-phthalimido-1-thia-3,8-diazaspiro[4.5]decane-2-acetate (obtained in 3.1) in 730 ml of dioxan are added 13.4 g of hydrazine hydrate. After 24 hours, a further 6 g of hydrazine hydrate are added, followed by filtration after 24 hours. The mixture is evaporated and the residue is dissolved in 1 liter of benzene, then filtered after 24 hours and the new residue obtained by evaporation is passed through a column of silica gel (60 Merck), using a 91 v/v benzene-methanol mixture as eluent. In this way, a solution of tert-butyl alpha-amino-4-benzyloxycarbonyl-8-methyl-1-thia-3,8-diazaspiro[4.5]decane-2-acetate is obtained, which is subjected as much to step 5.1.

4.2. tert-Butyl alpha-amino-8-benzyl-4-benzyloxycarbonyl-1-thia-3,8-diazaspiro-[4.5]decane-2-acetate.

To a solution of 42 g (0.065 mole) of tert-butyl 8-benzyl-4-benzyloxycarbonyl-alpha-phthalimido-1-thia-3,8-diazaspiro[4.5]decane-2-acetate (obtained in 3.2) in 300 ml of dioxan are added 8 g (0.155 mole) of hydrazine hydrate. The mixture is filtered after 4 days, the filtrate is evaporated to dryness and the residue is taken up in 600 ml of benzene.

After 24 hours, it is filtered, the filtrate is again evaporated to dryness and the residue is crystallized from acetonitrile. In this way, tert-butyl alpha-amino-8-benzyl-4-benzyloxycarbonyl-1-thia-3,8-diazaspiro[4.5]decane-2-acetate is obtained in a yield of 80%; M.P. 140°–141° C. Infra-red spectrum (KBr): 3340 cm$^{-1}$ (NH)

Mass spectrum: M$^+$·m/e=511; [M+H]$^+$·m/e=512

Analysis for C$_{28}$H$_{37}$N$_3$O$_4$S (M.W. 511.694): calculated (%): C 65.72; H 7.28; N 8.21; found (%): C 66.34; H 7.20; N 8.26

4.3. tert-Butyl alpha-amino-4-benzyloxycarbonyl-8-phenyl-1-thia-3,8-diazaspiro-[4.5]decane-2-acetate.

18.6 g (0.03 mole) of tert-butyl 4-benzyloxycarbonyl-8-phenyl-alpha-phthalimido-1-thia-3,8-diazaspiro[4.5]-decane-2-acetate (obtained in 3.3) are suspended in 50 ml of N,N'-dimethylformamide. A solution containing 2 g (0.04 mole) of hydrazine hydrate in 20 ml of N,N-dimethylformamide is added dropwise at 0° C. under an atmosphere of nitrogen. The reaction mixture is allowed to warm up to ambient temperature and stirred for 1 hour. The reaction mixture is then again cooled to 0° C. and slowly neutralized by the addition of 33.75 ml of 1N hydrochloric acid, whereafter it is stirred at ambient temperature for 2 hours after which time it solidifies. 300 ml of water are added, followed by extraction with chloroform. The organic phase is washed with water, dried with anhydrous sodium sulfate and evaporated to dryness. The residue is triturated with diethyl ether, filtered and the precipitate washed with diethyl ether. There are obtained 12.8 g of tert-butyl alpha-amino-4-benzyloxycarbonyl-8-phenyl-1-thia-3,8-diazaspiro[4.5]decane-2-acetate.

Yield: 86.7%; M.P. 167°–168° C. (decomposition).

IR spectrum (KBr) in cm$^{-1}$: 3480, 3425 (NH$_2$), 1720 (CO), 760 (phenyl).

Analysis for C$_{27}$H$_{35}$N$_3$O$_4$S (M.W. 497.64): calculated (%): C 65.16; H 7.09; N 8.44; Cl$^-$nil; found (%); C 63.92; H 7.10; N 8.83; Cl

Step (5)

5.1. alpha-Amino-4-benzyloxycarbonyl-8-methyl-1-thia-3,8-diazaspiro[4.5]decane-2-acetic acid dihydrochloride.

After evaporating the solution of tert-butyl alpha-amino-4-benzyloxycarbonyl-8-methyl-1-thia-3,8-diazaspiro[4.5]decane-2-acetate obtained in 4.1., the residue is dissolved in 1 liter of nitromethane, the solution is cooled to 0° C. and a current of gaseous hydrogen chloride is passed in for 1.5 hours. The product is left to stand for 2 hours at 0° C., then excess of solvent and hydrogen chloride is evaporated in vacuo at 30° C., replacing the nitromethane by isopropyl alcohol. The precipitate is filtered and dried to give 40.2 g of alpha-amino-4-benzyloxycarbonyl-8-methyl-1-thia-3,8-diazaspiro[4.5]decane-2-acetic acid dihyrochloride; Yield: 44.4%; M.P. 171°–172° C.

Mass spectrum: no M$^+$·, but M-44 (CO$_2$): m/e=335.

Analysis for $C_{18}H_{25}N_3O_4S \cdot 2HCl$ (M.W.: acid=379.488; dihydrochloride=452.418): calculated (%): C 47.79; H 6.02; N 9.29; S 7.09; Cl⁻15.67; found (%): C 46.01; H 5.97; N 9.09; S 6.82; Cl 15.44

5.2. alpha-Amino-8-benzyl-4-benzyloxycarbonyl-1-thia-3,8-diazaspiro[4.5]decane-2-acetic acid dihydrochloride.

The preparation is the same as in 5.1. except that the residue is taken up in benzene instead of in isopropyl alcohol. 56.5 g of dihydrochloride of the desired acid are obtained; Yield: 91.1%; M.P. about 175° C. (decomposition).

NMR spectrum: (CDCl₃-TMS):
HOOC-CH<: doublet at 5.25 ppm
H₂: doublet at 4.08 ppm
H₄: singlet at 3.65 ppm Analysis for $C_{24}H_{29}N_3O_4S \cdot 2HCl$ (M.W.: acid=455.586; dihydrochloride=528.516): calculated (%): C 54.54; H 5.91; N 7.95; Cl⁻13.41; found (%): C 52.36; H 5.97; N 7.57; Cl 13.19

5.3. alpha-Amino-4-benzyloxycarbonyl-8-phenyl-1-thia-3,8-diazaspiro[4.5]decane-2-acetic acid dihydrochloride.

A stream of gaseous hydrogen chloride is passed through a suspension of 11 g (0.0206 mole) of tert-butyl alpha-amino-4-benzyloxycarbonyl-8-phenyl-1-thia-3,8-diazaspiro[4.5]decane-2-acetate (obtained in 4.3) in 200 ml of nitromethane. After 1 hour, a clear solution is obtained which is filtered through "Hyflocel" and the filtrate is evaporated to dryness. The residue is taken up in diethyl ether, filtered and washed with diethyl ether. There are obtained 9.4 g of alpha-amino-4-benzyloxycarbonyl-8-phenyl-1-thia-3,8-diazaspiro[4.5]decane-2-acetic acid dihydrochloride. Yield: 95.5%; M.P. 164°-167° C. (decomposition).

IR spectrum (KBr) in cm⁻¹:1730 (CO); 755 (phenyl).

Analysis for $C_{23}H_{27}N_3O_4S \cdot 2HCl$ (M.W. 514.54): calculated (%): C53.69; H 5.68; N 8.17; Cl⁻13.78; found (%): C 51.55; H 5.83; N 7.84; Cl 12.92

STEP 6

6.1. 4-Benzyloxycarbonyl-8-methyl-alpha-tritylamino-1-thia-3,8-diazaspiro[4.5]-decane-2-acetic acid.

53.91 g (0.118 mole) of alpha-amino-4-benzyloxycarbonyl-8methyl-1-thia-3,8-diazaspiro[4.5]decane-2-acetic acid dihydrochloride (obtained in 5.1) and 98.7 g (0.354 mole) of trityl chloride are suspended in 1.2 liter of dichloromethane cooled to −10° C. and the suspension is slowly treated over the course of half an hour with 95.5 g of triethylamine. The reaction mixture is kept at 0° C. for 2 to 3 hours, then left to stand overnight at ambient temperature.

After filtration, washing with water and drying over anhydrous sodium sulfate, the solution is evaporated in vacuo. The evaporation residue is suspended in isopropyl alcohol and stirred mechanically for 15 hours. It is then filtered and the filter cake is dried. In this way, 88 g of 4-benzyloxy-carbonyl-8methyl-alpha-tritylamino-1-thia-3,8-diazaspiro[4.5]decane-2-acetic acid is obtained, which contains triphenylmethanol as an impurity. This product is used as such in the following step 7.1.

6.2.8-Benzyl-4-benzyloxycarbonyl-alpha-tritylamino-1-thia-3,8-diazaspiro[4.5]-decane-2-acetic acid.

This is prepared as in 6.1, starting from alpha-amino-8-benzyl-4-benzyloxy-carbonyl-1-thia-3,8-diazaspiro[4.5]decane-2-acetic acid dihydrochloride obtained in 5.2; 80 g of the required acid is obtained which contains triphenylmethanol as an impurity. This product is used as such in the following step 7.2; M.P. 148-149° C.

6.3. 4-Benzyloxycarbonyl-8phenyl-alpha-tritylamino-1-thia-3,8-diazaspiro[4.5]-decane-2-acetic acid.

9.1 g (0.0177 mole) of alpha-amino-4-benzyloxycarbonyl-8-phenyl-1-thia-3,8-diazaspiro[4.5]decane-2-acetic acid dihydrochloride (obtained in 5.3) are suspended in 150 ml of dichloromethane. After cooling to −20° C., 18,6 g (0.0668 mole) of trityl chloride are added all at once. While maintaining the temperature at about −20° C., the suspension is slowly treated over the course of 1 hour with 17.6 g (0.17 mole) of triethylamine in 100 ml of dichloromethane. The reaction mixture is stirred for 1 hour at a temperature of from −10 to −20° C. and then left to stand overnight in a refrigerator, whereafter it is poured onto an ice-water mixture (pH about 11) and neutralized to about pH 6 by the addition of 85% phosphoric acid. The aqueous phase is extracted three times with 100 ml of dichloromethane. The combined extracts are washed with water and dried over anhydrous sodium sulfate, followed by evaporation to dryness under high vacuum on a waterbath at a temperature of from 20° to 25° C. The 4-benzyloxycarbonyl-8-phenyl-alpha-tritylamino-1-thia-3,8-diazaspiro[4.5]-decane-2-acetic acid thus obtained is used, without further purification, in step 7.3.

STEP (7)

7.1. Benzyl 1'-methyl-6-tritylamino-spiro[penam-2,4'-piperidine]-3-carboxylate.

A mixture of 88 g of 4-benzyloxycarbonyl-8-methyl-alpha-tritylamino-1-thia-3,8-diazaspiro[4.5]decane-2-acetic acid (obtained in 6.1) and of 88 g of diisopropylcarbodiimide is left to stand in 300 ml of chloroform for 3 weeks at ambient temperature. After filtration and evaporation in vacuo of excess solvent and reagent, the residue is passed through a column of silica gel (60 Merck), using chloroform as eluent. After two passages, 25.2 g of the required compound are obtained, contaminated with 1,3-diisopropylurea. Combining the eluates and concentrating them to dryness gives benzyl 1'-methyl-6-tritylamino-spiro[penam-2,4'-piperidine]-3-carboxylate; yield: 35%. Infra-red spectrum (KBr) in cm⁻¹:3342 (NH); 1785 (beta-lactam; 1745 (ester).

NMR spectrum (CDCl₃-TMS):

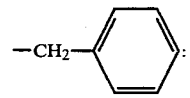

singlet at 5.12 ppm
H₃: singlet at 4.60 ppm
H₅ : doublet at 4.35 ppm
H₆ : doublet at 4.43 ppm
H₅ and ₆ are coupled, J=4.1 Hz
Mass spectrum: M⁺. m/e=603.

7.2. Benzyl 1'-benzyl-6-tritylamino-spiro[penam-2,4'-piperidine]-3-carboxylate.

The reation between 8 benzyl-4-benzyloxycarbonyl-alpha- tritylamino-1-thia-3,8-diazaspiro[4.5 ]decane-2-acetic acid (obtained in 6.2.) and diisopropylcarbodiimide (80 g) can be performed in chloroform (400 ml), dichloromethane or a mixture of nitromethane and chloroform, either at ambient temperature, leaving the mixture to stand for 4 weeks, or at 50° C. for 12 hours. In all cases, the 1,3-diisopropylurea formed is removed by filtration, the solvent and excess reagent are evaporated and the residue is evaporated and the residue is passed through a column of silica gel (60 Merck), using chloroform as eluent. In all cases, benzyl 1°-benzyl-6-tritylamino-spiro[penam-2,4'-piperidine ]-3-carboxylate is obtained, which is crystallized from diethy ether in a yield of 25 to 40%; M.P. 191°–192° C. (recrystallized from acetonitrile).

Infra-red spectrum (KBr) in cm$^{-1}$:3320 (NH); 1790 (beta-lactam); 1750 (ester).

NMR spectrum (CDCl$_3$-TMS:

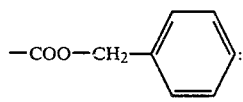

singlet at 5.50 ppm.

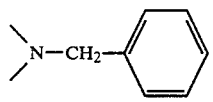

singlet at 4.12 ppm
H$_3$: singlet at 4.50 ppm
H$_5$: doublet at 4.32 ppm
H$_6$: doublet at 4.39 ppm H$_5$ and H$_6$ are coupled, J=4 Hz Mass spectrum:M$^+$·m/e=679

Analysis for C$_{43}$H$_{41}$N$_3$O$_3$S (M.W. 679.891): calculated (%): C 75.92; H 6.08; N 6.18; S 4.71; found (%): C 78.00; H 6.01; N 6.56; S 4.39

7.3. Benzyl 1'-phenyl-6-tritylamino-spiro[penam-2,4'-piperidine]-3-carboxylate.

To 32 g of crude 4-benzyloxycarbonyl-8-phenyl-alpha-tritylamino-1-thia-3,8-diazaspiro[4.5]decane-2-acetic acid, isolated in the preceding step (6.3), suspended in 150 ml of anhydrous nitromethane, is added dropwise a solution of 10 g (0.079 mole) of diisopropyl-carbodiimide in 50 ml of dichloromethane. The reaction is stirred overnight at ambient temperature. The solvent is evaporated off under vacuum at a waterbath temperature of 25° C. The residue is washed with hexane and chromatographed on a silica column using benzene and then chloroform as eluents. There are obtained 7.74 g of benzyl 1'-phenyl-6-tritylamino-spiro- [penam-2,4'-piperidine]-3-carboxylate. Yield: 61% (for the two consecutive steps 6.3 and 7.3); M.P. 200°–201° C.

IR spectrum (KBr) in cm$^{-1}$:1775 (beta-lactam CO); 1745 (ester)

Analysis for C$_{42}$H$_{39}$N$_3$O$_3$S (M.W. 665.82): calculated (%): C 75.76; H 5.90; N 6.31; found (%): C 76.74; H 5.82; N 6.30

Step (8)

8.1. Benzyl 6-amino-1'-methyl-spiro[penam-2,4'-piperidine]-3-carboxylate di-p-toluenesulfonate.

A mixture of 16 g (0.0266 mole) of benzyl 1'-methyl-6-tritylamino-spiro-[pename-2,4'-piperidine]-3-carboxylate (obtained in 7.1) and of 10.12 g (0.053 mole) of p-toluene-sulfonic acid is stirred for four hours at ambient temperature in 160 ml of acetone. After filtration and drying, 15 g (79.9% yield) of benzyl 6-amino-1'-methyl-spiro[penam-2,4'-piperidine]-3-carboxylate di-p-toluenesulfonate are obtained; M.P. 182°–183° C.

Infra-red spectrum (KBr) in cm$^{-1}$: 2930 (NH$_3^{30}$ ); 1794 (beta-lactam); 1745 (ester)

NMR spectrum (DMSO-TMS):
H$_3$: singlet at 4.98 ppm
H$_5$: doublet at 5.18 ppm
H$_6$: doublet at 5.57 ppm
H$_5$ and H$_6$ are coupled, J=4.1 Hz Analysis for C$_{32}$H$_{39}$N$_3$O$_9$S$_3$(M.W.: base=361.472; salt=705.886): calculated (%): C 54.45; H 5.57; N 5.95; S 13.62; found (%): C 54.12; H 5.54; N 5.98; S 13.46

8.2. Benzyl 6-amino-1'-benzyl-spiro[penam-2,4'-piperidine]-3-carboxylate di-p-toluenesulfonate.

18.7 g (0.027 mole) of benzyl 1'-benzyl-6-tritylamino-spiro[penam-2,4'-piperidine]-3-carboxylate (obtained in 7.2.) are stirred at ambient temperature with 10.3 g of p-toluenesulfonic acid in 100 ml of acetone. The reaction mixture is filtered after 5 hours and the residue is dried; yield: 80%; M.P. approx. 158° C. (decomposition).

Infra-red spectrum (KBr) in cm$^{-1}$: 1790 (beta-lactam); 1740 (ester) NMR spectrum (DMSO-TMS):

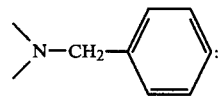

singlet at 4.38 ppm
H$_3$: singlet at 4.55 ppm

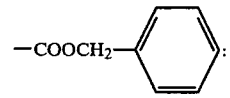

singlet at 5.20 ppm
H$_5$: doublet at 5.20 ppm
H$_6$: doublet at 5.56 ppm H$_5$ and H$_6$ are coupled, J=5.3 Hz Mass spectrum: no M$^+$; m/e=381:

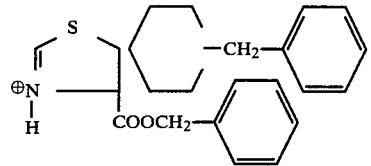

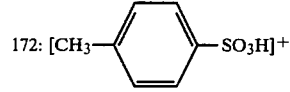

Analysis for C$_{24}$H$_{27}$N$_3$O$_3$S. 2 C$_7$H$_8$O$_3$S (M.W.: base=437.570; salt=781.984): calculated (%): C 58.37; H 5.54; N 5.37; S 12.30; found (%): C 57.78; H 5.69; N 5.37; S 11.92

8.3. Benzyl 6-amino-1'-phenyl-spiro[penam-2,4'-piperidine]-3-carboxylate di-p-toluenesulfonate.

A mixture of 1.33 g (0.002 mole) of benzyl 1'-phenyl-6-tritylamino-spiro [penam-2,4'-piperidine]-3-carboxylate (obtained in 7.3) and 0.76 g of p-toluenesulfonic acid in 10 ml of acetone is stirred at ambient temperature for 6 hours. After filtering and drying, there is obtained 1.40 g of benzyl 6-amino-1'-phenyl-spiro[penam-2,4'-piperidine]-3-carboxylate di-p-toluenesulfonate. Yield: 92%; M.P. 168°–169° C. (decomposition).

IR spectrum (KBr) in cm$^{-1}$: 1785 (CO beta-lactam); 1732 (ester)

Analysis for $C_{37}H_{41}N_3O_8S_3$ (M.W. of salt: 767.92): calculated (%): C 57.87; H 5.38; N 5.47; found (%): C 57.49; H 5.54; N5.19

Step (9).

9.1. 6-Amino-1'-methyl-spiro[penam-2,4'-piperidine]-3-carboxylic acid di-p-toluenesulfonate.

A solution of 2.5 g (0.00354 mole) of benzyl 6-amino-1'-methyl-spiro[penam-2,4'-piperidine]-3-carboxylate di-p-toluenesulfonate (obtained in 8.1) in 1.5 liter of ethanol is subjected to hydrogenolysis in a Parr's apparatus under 3.2 kg/cm² of hydrogen in the presence of 2 g of palladium on carbon (10% Pd). After 90 minutes, the reaction mixture is filtered and the filtrate is evaporated to dryness and lyophilized in 600 ml of water. 1.8 g of 6-amino-1'-methyl-spiro[penam-2,4'-piperidine]-3-carboxylic acid di-p-toluenesulfonate is obtained; yield: 83%; M.P. approx 155°-160° C. (start of decomposition).

Infra-red spectrum (KBr) in cm$^{-1}$: 2920 ($NH_3^{30}$); 1795 (beta-lactam); 1730 (carboxyl)

NMR spectrum ($D_2O$-DSS):
 $H_5$: doublet at 5.15 ppm
 $H_6$: doublet at 5.70 ppm
 $H_5$ and $H_6$ are coupled, J=4.1 Hz Analysis for $C_{25}H_{33}N_3O_9S_3$ (M.W.:acid=271.355-;salt=615.769): calculated (%):C 48.76; H 5.40; N 6.82; S 15.62; found (%):C 44.71; H 5.86; N 6.07; S 14.27

9.2. 6-Amino-1'-benzyl-spiro[penam-2,4'-piperidine ]-3-carboxylic acid di-p-toluenesulfonate.

The preparation is the same as in 9.1, starting from benzyl 6-amino-1'-benzyl-spiro[penam-2,4'-piperidine ]-3-carboxylate di-p-toluenesulfonate; yield: 67.4%; M.P. decomposition towards 115°-120° C.

Infra-red spectrun (KBr) in cm$^{-1}$:2930 ($NH_3^+$);1790 (beta-lactam); 1735 (carboxyl)

NMR spectrum (DMSO-TMS):

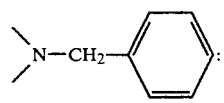

singlet at 4.4 ppm
 $H_3$: singlet at 4.67 ppm
 $H_5$: doublet at 5.15 ppm
 $H_6$: doublet at 5.53 ppm
 $H_5$ and $H_6$ are coupled, J=4.7 Hz (approx)

Analysis for $C_{17}H_{21}N_3O_3S.2C_7H_8O_3S$ (M.E.: acid=347.445; salt=691.859): calculated (%):C 53.80; H 5.39; N 6.07; found (%):C 52.05; H 5.65; N6.00

9.3. 6-Amino-1'-phenyl-spiro[penam-2,4'-piperidine]-3-carboxylic acid di-p-toluenesulfonate.

Hydrogenation is carried outas in 9.1, starting from benzyl 6-amino-1'-phenyl-spiro[penam-2.4'-piperidine]-3-carboxylate di-p-toluenesulfonate.

Yield: 38%; M.P. 228°-230° C. (decomposition)

IR Spectrum (KBr) : 1785 cm$^{-1}$ (CO beta-lactam)

NMR spectrum (DMSO-TMS):
 $H_3$: singlet at 4.67 ppm
 $H_5$: doublet at 5.13 ppm
 $H_6$: doublet at 5.53 ppm
 $H_5$ and $H_6$ are coupled, J=4.4 Hz Analysis for $C_{30}H_{35}N_3O_9S_3$ (M.W. of salt 677.80): calculated (%): C 53.16; H 5.20; N 6.20; found (%): C 48.88; H 4.92; N 6.02.

Example 2. Preparation of a compound analogous to penicillin G.

2.1 Benzyl 1'-methyl-6-(2-phenylacetamido)-spiro[penam-2,4'-piperidine]-3-carboxylate.

The benzyl 6-amino-1'-methyl-spiro[penam-2,4'-piperidine]-3-carboxylate di-p-toluenesulfonate (8.5 g=0.012 mole) described in Example 1.8.1 is converted into the free base by dissolving it in 200 ml of dichloromethane and adding 2.44 g (0.024 mole) of triethylamine. The solution is cooled to −10° C. and is treated simultaneously with a solution of 1.86 g (0.012 mole) of phenylacetyl chloride in 40 ml of dichloromethane and with a solution of 1.24 g (0.012 mole) of triethylamine in 40 ml of dichloromethane, the addition taking approximately 1 hour.

Stirring is continued for 2 hours, allowing the temperature to return to 0° C., then the solution is washed successively with water, a saturated solution of sodium hydrogen carbonate and again with water. After evaporating to dryness, 4.4 g of benzyl 1'-methyl-6-(2-phenylacetamido)-spiro[penam-2,4'-piperidine]-3-carboxylate are obtained; yield: 76.2%; M.P. 124°-125° C.

Infra-red spectrum (KBr) in cm$^{-1}$: 3318 (NH); 1800 (beta-lactam); 1740 (ester); 1670 (amide); 690, 740 (monosubstituted phenyl)

NMR spectrum ($CDCl_3$-TMS):
 $H_3$: singlet at 4.52 ppm
 $H_5$: doublet at 5.47 ppm
 $H_6$: doublet at 5.65 ppm
 $H_5$ and $H_6$ are coupled, J=4.1 Hz Mass spectrum: M+· m/e=479.

2.2. 1'-Methyl-6-(2-phenylacetamido)-spiro[penam-2,4'-piperidine]-3-carboxylic acid.

Under a hydrogen pressure of 3.2 kg/cm² and in the presence of 4.4 g of palladium on carbon (10% Pd), a solution of 4.4 g (0.091 mole) of benzyl 1'-methyl-6-(2-phenylacetamido)-spiro[penam-2,4'-piperidine]-3-carboxylate (prepared in 2.1.) in 800 ml of ethanol is hydrogenolyzed in a Parr's apparatus for 1 hour. It is then filtered and the precipitate is digested in 1.5 liter of a 9:1 v/v methanol-water mixture for 1 hour. Evaporation of the filtrate to dryness gives 1.6 g of 1'-methyl-6-(2-phenylacetamido)-spiro[penam-2,4-piperidine]-3-carboxylate acid; yield: 44.8%; M.P. 189°-190° C. (decomposition).

Infra-red spectrum (KBr): 1770 cm$^{-1}$ (beta-lactam)

Mass spectrum: M—44 ($CO_2$): m/e=345

Analysis for $C_{19}H_{23}N_3O_4S$ (M.W. 389.483): calculated (%): C 58.59; H 5.95; N 10.78; S 8.23; found (%): C 56.7; H 6.1; N 10.20; S 7.20.

Pharmacological properties.

Various comparative tests have been carried out in order to ascertain the intrinsic biological activity of the compounds of general formula (I) against various bacterial strains of the Gram-positive and Gram-negative type. Generally speaking, bacteria can offer resistance to antibiotics by two mechanisms:

(1) by liberating a beta-lactamase which hydrolyzes the lactam ring of the antibiotic; in the positive case, this is indicated by P+ and in the negative case by P−;

(2) by impermeability of the bacterial cell wall towards the antibiotic; in the positive case, this is indicated by I+ and in the negative case by I−.

First of all, information is given concerning the origin and characteristics of the bacterial strains used.

Gram-positive bacterial strains.

*STAPHYLOCOCCUS AUREUS* 6538 (P⁻) (I⁻)

This is a Gram-positive coccus which is particularly sensitive to penicillins and which has a low resistance mechanism. This strain of Staphylococcus is, therefore, representative of a maximum sensitivity of the species.

*STAPHYLOCOCCUC AUREUS* 52149 (P+) (I⁻)

This is a Gram-positive coccus, the intrinsic sensitivity of the receptor of which is equivalent to that of the preceding strain but which produces a beta-lactamase typical of the species which renders it resistant to all penicillins sensitive to hydrolysis.

Gram-negative bacterial strains.

*ESCHERICHIA COLI* B. (P⁻) (I⁻)

This is a well-known collection strain of Escherichia coli which produces very little beta-lactamase (of type I) and is, therefore, very sensitive to penicillins. Regarding the classification of the beta-lactamases, use is here made of that proposed by M. H. RICHMOND and R. B. SYKES in Advances in Microbial Physiology, 9, (1973), 43 and 45.

*ESCHERICHIA COLI* B-AMPI R (P+) (I⁻)

This is a mutant of the preceding strain, which we have produced. This strain is, on the contrary, a hyper-producer of the type I beta-lactamase already produced by the parent strain Escherichia coli B. It has an increased resistance to the penicillins, which would appear to be directly connected with the production of the beta-lactamase.

*ESCHERICHIA COLI* B (P⁻) (I+)

Pleiotropic mutant produced from *E. coli* B; resistant to penicillins due to hyper-impermeability.

*ESCHERICHIA COLI* K12 (P⁻) (I⁻)

Well-known collection strain; weak producer of a type I beta-lactamase; very sensitive to penicillins.

*ESCHERICHIA COLI* K12-z(P⁻) (I⁻)

Pleiotropic mutant of the preceding strain; highly sensitive to penicillins due to increased permeability.

*ESCHERICHIA COLI* K12-4 (P⁻) (I+)

Pleiotropic mutant of *E. coli* K12; resistant to penicillins due to impermeability.

*ESCHERICHIA COLI* K12-44 (P⁻) (I⁻) p Mutant which does not produce beta-lactamase; obtained from a strain of *E. coli* K12.

*ESCHERICHIA COLI* K12-44-S (P⁻) (I⁻)

Pleiotropic mutant obtained from *E. coli* K12-44; does not produce beta-lactamase and is very sensitive to the penicillins due to hyper-permeability.

*ESCHERICHIA COLI* K12-44-R (P⁻) (I+)

Pleiotropic mutant obtained from *E. coli* K12-44; does not produce beta-lactamase and is resistant to the penicillins due to impermeability.

N.B.: the episomes TEM, RP$_1$, RP$_1$* have been transferred to various strains of the *E. coli* K12-44 series, which become, for example

*E. COLI* K12-44-TEM
*E. COLI* K12-44-S-TEM
*E. COLI* K12-44-R-TEM

The episome TEM is, in particular, responsible for the production of a beta-lactamase of type III (P+). The episome RP$_1$ is more particularly responsible for the production of a beta-lactamase of type III (P+) and of a penicillin-resistance factor attributed to impermeability (I+). The episome RP$_1$* is a modified form of the preceding which no longer determines the production of the beta-lactamase (P⁻) but has retained the impermeability factor (I+).

*AEROBACTER CLOACAE* P99 (P+)(I⁻)

Is a typical strain of this species; it is characterized by the abundant production of a type I beta-lactamase.

*AEROBACTER CLOACAE* 1321 E (P⁻) (I⁻)

Is a mutant of *A. cloacae* P99 which does not produce beta-lactamase.

*KLEBSIELLA AEROGENES* 1082 E (P+)(I⁻)

Typical strain of the spcies; produces a type IV beta-lactamase.

*KLEBSIELLA AEROGENES* K1 (P⁻) (I⁻)

This is a mutant of *K. aerogenes* 1082 E not producing beta-lactamase.

Comparative activity tests.

In Table I hereinbelow, the antibacterial activity of 6-amino-1'-methyl-spiro[penam-2,4'-piperidine]-3-carboxylic acid di-p-toluenesulfonate obtained in 9.1. (called A.9.1. for short) and of 6-amino-1'-benzyl-spiro[penam-2,4'-piperidine]-3-carboxylic acid di-p-toluenesulfonate obtained in 9.2 (called A.9.2. for short) is compared with that of the homologous 6-aminopenicillanic acid (6-APA for short) which is the basis of all the penicillins and which differs from A.9.1. and A.9.2. only in the presence in the 2-position of a gem-dimethyl group (instead of 3-azapentamethylene groups which is characteristic of the compounds of the present invention). At the same time, a comparison is made with the activity of ampicillin (AMPI for short) which is a well-known penicillin. For the foour compounds which are the subject of the comparison, the minimum inhibitory concentration (MIC for short) of the growth of bacteria is determined, this concentration being expressed in micromoles/ml and is determined by the following method.

The products to be tested are introduced, in increasing concentrations, into a gelose culture medium in Petri dishes. A multiple inoculator is used to deposit simultaneously drops (making 10 microliters in all) of inoculum (suspension of about 10⁵ bacteria per ml) on to the surface of the medium. After incubation at 37° C. for 24 hours, the growth of the bacteria is observed. By definition, the MIC is expressed by the minimum concentration which inhibits the multiplication of the bacteria.

TABLE I

| Bacterial strain | A.9.1. | A.9.2. | 6-APA | AMPI |
|---|---|---|---|---|
| Gram-positive: | | | | |
| *S.AUREUS* 6538 (P⁻)(I⁻) | 16 | 16 | 250–500 | 0.06 |
| *S.AUREUS* 52149 (P+)(I⁻) | 16 | 16 | 250–500 | 4 |
| Gram-negative: | | | | |
| *E.COLI* B (P⁻)(I⁻) | 4 | 8 | 62 | 4 |
| *E.COLI* B-c (P⁻)(I+) | 8 | 31 | 62–125 | 125 |
| *E.COLI* B-AMPI R (P+)(I⁻) | 8 | 125 | 125 | 125 |
| *E.COLI* K12-z (P⁻)(I⁻) | 4–8 | 8 | 62 | 4 |
| *E.COLI* K12 (P⁻)(I⁻) | 8 | 16 | 62 | 8 |

TABLE I-continued

| Bacterial strain | A.9.1. | A.9.2. | 6-APA | AMPI |
|---|---|---|---|---|
| E.COLI K12-4 (P⁻)(I⁺) | 4–8 | 125 | 62 | 125 |
| E.COLI K12-44-S (P⁻)(I⁻) | 8 | 16 | 125 | 1 |
| E.COLI K12-44-S-RP₁* (P⁻)(I⁺) | 8 | 62 | >500 | 500 |
| E.COLI K12-44-S-TEM (P⁺)(I⁻) | 31 | 250 | >500–100 | 1000 |
| E.COLI K12-44-S-RP₁ (P⁺)(I⁺) | 62 | 500 | 500–1000 | >1000 |
| E.COLI K12-44 (P⁻)(I⁻) | 8 | 16 | 62–125 | 4 |
| E.COLI K12-44-RP₁* (P⁻)(I⁺) | 31 | 500 | >1000 | >1000 |
| E.COLI K12-44-TEM (P⁺)(I⁻) | 31 | 250 | >1000 | >1000 |
| E.COLI K12-44-RP₁ (P⁺)(I⁺) | 62 | 500 | >1000 | >1000 |
| E.COLI K12-44-R (P⁻)(I⁺) | 8 | 62 | 62–125 | 125 |
| E.COLI K12-44-R-RP₁* (P⁻)(I⁺) | 16 | 62 | 500 | >1000 |
| E.COLI K12-44-R-TEM (P⁺)(I⁺) | 31 | 250 | >1000 | >1000 |
| E.COLI K12-44-R-RP₁ (P⁺)(I⁺) | 125 | >1000 | >1000 | >1000 |
| A.CLOACAE 1321 E (P⁻)(I⁻) | 8 | 16 | 62 | 8 |
| A.CLOACAE P99 (P⁺)(I⁻) | 8 | 16 | 62 | >1000 |
| K.AEROGENES K1 (P⁻)(I⁻) | 16 | 16 | 62–250 | 4 |
| K.AEROGENES 1082E (P⁺)(I⁻) | 250 | 1000 | >500–2000 | >1000 |

From Table I, it can clearly be seen that the compounds A.9.1. and A.9.2. according to the present invention are active at much lower concentrations than the prior art compound 6-APA, both against bacteria which release a beta-lactamase and against those which develop impermeability towards the antibiotic tested. Furthermore, against Gram-negative bacteria, the compounds A.9.1. and A.9.2. have an activity which is far superior to that of the known penicillin ampicillin.

It follows from these results that the compounds of general formula (I) according to the present invention can be used as antibacterial agents and as therapeutic agents for man and animals in the treatment of infectious diseases caused by Gram-positive and Gram-negative bacteria. In particular, they are highly effective for combating resistant Gram-negative strains of bacteria, whatever the type of resistance presented by the bacteria, i.e. by liberation of beta-lactamases and/or by impermeability of the cell wall.

For these uses, the compounds of general formula (I) can be administered orally or parenterally, in doses comparable to those currently used for ampicillin (0.7 to 7 g per day), these doses being, of course, liable to adaptation in function of the patient and of the disease to be treated. The new compounds can be administered in admixture with the usual solid or liquid pharmaceutical diluents or carriers.

We claim:

1. A 6-amino-spiro[penam-2,4'-piperidine]-3-carboxylic acid of the formula

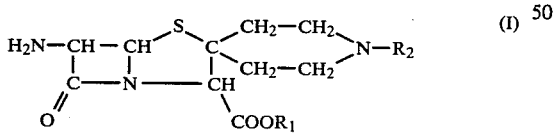

(I)

wherein $R_1$ is a hydrogen atom, benzyl or an alkali metal or ammonium ion and $R_2$ is a methyl, phenyl or benzyl or a pharmaceutically acceptable acid addition salt thereof.

2. A compound as claimed in claim 1, namely 6-amino-1'-methyl-spiro[penam-2,4'-piperidine]-3-carboxylic acid, its benzyl ester or the p-toluene-sulfonates thereof.

3. A compound as claimed in claim 1, namely 6-amino-1'-benzyl-spiro[penam-2,4-piperidine]-3-carboxylic acid, its benzyl ester or the p-toluene-sulfonates thereof.

4. A compound as claimed in claim 1, namely 6-amino-1'-phenyl-spiro[penam-2,4'-piperidine]-3-carboxylic acid, its benzyl ester or the p-toluene-sulfonates thereof.

5. An antibacterial composition which comprises a pharmaceutical carrier and an antibacterially effective amount of a 6-amino-spiro[penam-2,4'-piperidine]-3-carboxylic acid of the formula

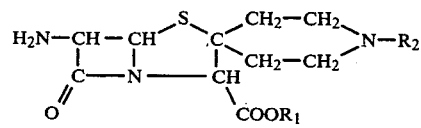

wherein $R_1$ is a hydrogen atom, benzyl or an alkali metal or ammonium ion and $R_2$ is a methyl, phenyl or benzyl radical or a pharmaceutically acceptable acid addition salt thereof.

6. A method of treating infectious diseases caused by Gram-positive and Gram-negative bacteria in warm-blooded animals, which comprises administering to said animals an antibacterially effective amount of a 6-amino-spiro[penam-2,4'-piperidine]-3-carboxylic acid of the formula

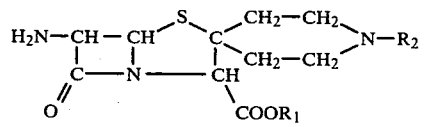

wherein $R_1$ is a hydrogen atom, benzyl or an alkali metal or ammonium ion and $R_2$ is a methyl, phenyl or benzyl radical or a pharmaceutically acceptable acid addition salt thereof.

* * * * *